United States Patent [19]
Gombinsky et al.

[11] Patent Number: 5,395,498
[45] Date of Patent: Mar. 7, 1995

[54] METHOD FOR SEPARATING BIOLOGICAL MACROMOLECULES AND MEANS THERFOR

[76] Inventors: Moshe Gombinsky, 10 Herzl St., Bat-Yam 59302, Israel; Adi Se-Lavan Lev, 9 Bar-Yehuda St., Nathanya 42344, Israel

[21] Appl. No.: 970,081

[22] Filed: Nov. 2, 1992

[30] Foreign Application Priority Data

Nov. 6, 1991 [IL] Israel ............ 99974
Oct. 1, 1992 [IL] Israel ............ 103312

[51] Int. Cl.⁶ ............................. C25B 7/00
[52] U.S. Cl. ................. 204/182.8; 204/299 R; 436/526
[58] Field of Search ......... 204/182.8, 299 R; 436/526

[56] References Cited

U.S. PATENT DOCUMENTS

| | | | |
|---|---|---|---|
| 4,169,804 | 10/1979 | Yapel, Jr. ............ | 436/526 |
| 4,554,088 | 11/1985 | Whitehead et al. ............ | 436/526 |
| 4,911,816 | 3/1990 | Love et al. ............ | 204/299 R |
| 4,994,166 | 2/1991 | Fernwood et al. ............ | 204/299 R |

OTHER PUBLICATIONS

Whitesides, G. M. et al., *Trends in Biotechnology*, 1(5) (1983).
Pourfarzaneh, M. et al., *Methods of Biochemical Analysis*, 28, 267–295 (1982).
Gershoni, J. M. et al., *Analytical Biochemistry*, 13 1, 1–15 (1983).
Smith, Hamilton O., *Methods in Enzymology*, 65, 371–380 (1980).
Gershoni et al., *Analytical Biochemistry*, 124, 396–405 (1982).
Peferoen, M. et al., *FEBS Letters*, 145(2), 369–372 (1982).
Hultman, T. et al., *Bio-Techniques*, 10(1), 84–93 (1991).
Gooderham, K., "Protein Blotting," *Techn. Molecular Biology*, J. M. Walber and W. Gastra (1983).
Vaclav Horejsi, *Methods in Enzymology*, 104, 275–281 (1984).

*Primary Examiner*—John Niebling
*Assistant Examiner*—C. Delacroix-Muirheid
*Attorney, Agent, or Firm*—Synnestvedt & Lechner

[57] ABSTRACT

Macromolecules from a sample are electrophoresed and the obtained electrophoretogram is contacted with a planar matrix of magnetic particles. The magnetic particles having binding specificity to one or more specific species of biological macromolecules, whereby the one or more specific macromolecules bind to the particles in the matrix. The particles can then be collected on the basis of their magnetic properties and the bound macromolecules can then be separated from the particles.

16 Claims, 4 Drawing Sheets

METHOD FOR SEPARATING BIOLOGICAL MACROMOLECULES AND MEANS THERFOR

FIELD OF THE INVENTION

The present invention concerns a method for isolating biological macromolecules such as proteins, polypeptides, glycoproteins or nucleic acids from electrophoretograms on which they were separated. The present invention makes use of a matrix of magnetic particles, having an affinity to the separated molecules. The present invention further concerns a kit for use in the above method, as well as methods for the preparation of the magnetic particles' matrix.

BACKGROUND OF THE INVENTION

Gel electrophoresis is one of the most convenient and widely used methods for separating proteins and nucleic acid molecules. The macromolecules separated on the gel are generally unaccessible to various probes which are required for analysis, and it is accordingly necessary to transfer the molecules from the gel to a suitable filter sheet so as to enable the probes' access to the separated molecules. The molecules adsorb to the filter sheet to which they immobilize while maintaining their respective position as in the gel—a process known as "blotting".

Suitable filter sheets used for blotting include nitrocellulose membranes, nylon filters, diazo-modified papers, cyanogen-bromide activated paper and ion-exchange paper. The transfer of the separated molecules to the filter sheet can be carried out by vacuum blotting, pressure blotting, electroblotting and capillary blotting. DNA molecules are usually blotted by means of pressure or vacuum, while protein molecules can also be blotted by the application of an electric field (electroblotting). (Gershoni J. M. et al., *Protein Blotting: Principles and Applications*, Analytical Biochemistry, 131, 1–15 (1983)).

After they are transferred to the filter sheet the macromolecules become accessible to probes, such as antibodies, nucleic acid probes and the like, and the identity of the macromolecule can thus be revealed. However, in order to recover macromolecules of interest from the filter sheet, the portion of the sheet containing the respective macromolecules must be cut from the sheet and the desired molecules are then eluted by suitable reagents. This recovery process presents several problems. First, it is not always simple to determine exactly the boundaries between different macromolecules on the sheet. Second, the use of an eluent necessarily dilutes the molecules.

The direct recovery of macromolecules from the gel by electroelution, gel dissolution, gel compression or diffusion also presents several problems. (Hamilton O. Smith, *Recovery of DNA front Gels.* Methods in Enzymology, Vol. 65, 371–380 (1980)). Recovery of micrograms or nanograms of DNA or protein from a gel weighing several milligrams is inherently a very difficult task and accordingly, all these procedures are very time and labor consuming. This problem is especially pronounced where a number of DNA or protein fractions have to be purified from a single sample.

The nature of the filter sheets currently used for blotting present several further problems. Nitrocellulose membranes have a relatively low binding capacity in the order of 80–100 $\mu$g protein/cm$^2$, which is a drawback where multiple probing is desired, as proteins are lost during washes between the contacts with the different probes and thus only one or very few washing and probing cycles are possible.

Nylon membranes generally have a higher capacity for proteins. For example, ZETABIND ™ (AMF Cuno Division, USA) or ZETAPROBE ™ (Bio-Rad Laboratories, USA) which is a nylon matrix which has been modified by extensive cationization, has a binding capacity of 480 $\mu$g protein/cm$^2$. This high binding capacity is also a problem, since areas of the nylon filter not occupied by the separated proteins can adsorb the probes non-specifically during the incubation period, which results in an intolerably high background signal. This may, at times, be avoided by saturating the filter's unbound sites by proteins such as BSA and hemoglobin.

Other filter sheets used such as diazo-modified papers (diazo-benzyl-oxymethyl paper, diazo-phenyl-thioether paper) cyanogen bromide activated paper and ion-exchange papers have a relatively low protein binding capacity in the order of 25–50 $\mu$g protein/cm$^2$. These filter sheets need to be activated prior to use and have in general a low resolution, which properties render them often unsuitable.

Magnetic particles are used for a variety of techniques based on affinity binding of molecules to the particles and then isolating the particles by application of a magnetic field. Such magnetic separations have been employed to sort cells, to recover antibodies or enzymes from solutions, to purify proteins using affinity techniques and to remove unwanted particles from suspensions (Pourfarzaneh M. K. et al., *The Use of Magnetizable Particles in Solid Phase Immunoassay in Methods of Biochemical Analysis*, Vol. 28, pp 267–275 (1982)).

SUMMARY OF THE INVENTION

In the following description and claims the term "*magnetic particles*" will be used to denote particles of various sizes, comprising a magnetic substance, being a substance which is either a magnet, i.e. having a 'magnetic memory' or a substance which is not a magnet but is attracted to magnets, i.e. a ferromagnetic material. The magnetic particles may consist solely or essentially of the magnetic substance. Alternatively, the magnetic particles may be composite particles comprising the magnetic substance and other non-magnetic substances such as agar, agarose, non-magnetic metal, glass, nitrocellulose, etc. The composite particle may either consist of a core or made of the magnetic substance and a shell made of the non-magnetic substance or may comprise several sub-particles made of the magnetic substance embedded in the non-magnetic substance. The term "*magnetic particles*" is to be understood as encompassing also the so-called "*magnetic beads*" or "*magnetic microbeads*" used in the literature.

The present invention provides a novel method for isolating one or more specific species of biological macromolecules from a sample, comprising separating said macromolecules by electrophoresis, thereby obtaining an electrophoretogram of said macromolecules; characterized in that said electrophoretogram is contacted with a planar matrix of magnetic particles having binding specificity to the one or more specific species of biological macromolecules, whereby said one or more specific species bind to particles in the matrix at a location of the matrix which corresponds essentially to the location of said one or more specific species in said electrophoretogram.

The use of magnetic particles in which the magnetic substance is ferromagnetic is generally preferred. In the following the invention will be described with reference to the use of such particles although it will be appreciated that by obvious modification of the described embodiments, the invention can also be practiced by the use of magnetic particles in which the magnetic substance is a magnet.

The magnetic substance may be ferromagnetic, for example made of superparamagnetic iron oxide. Such particles are capable of responding well to relatively weak magnetic fields, but have essentially no magnetic memory, that is once the magnetic field is removed they do not maintain magnetic attraction forces. The particles can be coated by a coating which confers the binding specificity, such as for example: nitrocellulose coating or a coating which carries positively charged molecules which have a general affinity to almost all proteins; a glass coating which confers a general affinity to DNA; an external coating of poly-T or poly-U residues having an affinity to mRNA; an external lectin coating which confers a binding specificity to glycoproteins; a coating consisting of one member of a binding pair conferring a specific affinity to the other member of the binding pair, e.g. an antibody having specific affinity to a certain antigen, a ligand having an affinity to a receptor, an enzyme to a substrate, a complementary sequence of DNA to a DNA or RNA sequence, etc. The particles can also be non-coated where there exists an affinity between the ferromagnetic material and the macromolecules. The particles can also be composite particles, for example an agarose particle in which there are embedded one or more smaller particles made of ferromagnetic materials.

Once the electrophoretogram is contacted with the magnetic particles matrix the macromolecules having specific affinity to the magnetic particles, become immobilized on the matrix in a location of the matrix which corresponds essentially to the location of the macromolecules in the electrophoretogram. The particles from a specific location in the matrix may then be easily separated from the rest of the matrix. Thus, if the location of a specific species of macromolecules in the electrophoretogram, and hence also in the matrix, is known, e.g. after appropriately staining the magnetic particles' matrix by means well-known in the art, such as by enzymatic reactions, immuno reactions, use of fluorescent or radioactive labels and the like, the particles having this species attached thereto can then be easily collected from the matrix, e.g. by using a device having a tapered magnetic tip or the like. The macromolecules may then be dissociated from the separated magnetic particles by a variety of standard means.

The magnetic particles' matrix may be formed on a suitable planar substrate which can be a sheet capable of adsorbing or absorbing the particles, such as a nitrocellulose sheet, pergameneous sheet, cellulose acetate sheet, xerographic paper, etc. Alternatively, the matrix can be prepared on a rigid substance such as a glass, a flat iron plate or an inert plastic substance, in which case the particles can be immobilized onto said rigid substance by means of a magnet attached at its other side.

In accordance with another embodiment, the magnetic particles' matrix can also be integral with the gel used for electrophoresis, in which case the magnetic particles' matrix is formed in a layer of the gel which is different than the one in which the macromolecules are electrophoresed. The layer of the gel in which the electrophoresis takes place will be referred to herein as the "electrophoresis layer" and the layer wherein the magnetic particles are present will be referred to herein as the "matrix layer".

The embodiment in which the matrix of the magnetic particles is formed on a separate sheet, will be referred to herein at times as "non-integral matrix embodiment", and the embodiment in which the matrix of the magnetic particles is embedded in the gel used for electrophoresis will be referred to herein at times as "integral matrix embodiment".

When performing the non-integral matrix embodiment of the invention, the contact between the particles and the macromolecules is achieved by transferring the macromolecules to the magnetic particles matrix by standard blotting techniques routinely used in the art to transfer macromolecules from a gel to a separate sheet. (Gershoni, J. M. et al., *Anal. Biochem.*, 131 1–15 (1983); Peferoen M, *Febs Lett.*, 145 (2), 309–372 (1982); Gershoni, J. M. et al., *Anal. Biochem.*, 124, 396–405 (1982)).

When performing the integral matrix embodiment of the present invention, the transfer of the macromolecules to the magnetic particles matrix may be performed by inter-layer blotting, i.e. transfer of the macromolecules in the gel from the electrophoresis layer to the matrix layer, e.g. by the application, in a direction normal to the gel's surface, of an electric field, vacuum or pressure, etc. Alternatively, in accordance with the integral embodiment, the macromolecules and the particles are brought into contact with one another by utilizing the particles magnetic properties and dissolving or melting the gel in a controlled manner. In accordance with this mode of providing contact, a planar magnet is placed close to the surface of the gel which is near the electrophoresis layer. The gel is then melted, dissolved or enzymatically digested in a controlled manner so that the matrix layer is first and the electrophoresis layer is the last one to be dissolved, melted or digested. Owing to their magnetic attraction to the magnet, the particles are not washed away but rather move towards the electrophoresis layer with progress of the melting, or dissolution or digestion. Eventually the magnetic particles come into contact with the separated macromolecules in the electrophoresis layer, whereby the said one or more species of macromolecules bind thereto. The entire matrix of magnetic particles, bound to one or more species becomes eventually immobilized on the magnetic substrate. The location of the one or more species in the immobilized magnetic beads matrix corresponds essentially to the location this one or more species had in the electrophoretogram and so a replica of the species' location in the gel is formed by the particles immobilized on the magnetic substance. The melting or dissolution of the gel may be performed by heating the gel, e.g. by the use of a heating plate, by the use of appropriate solvents, or by use of enzymes which are capable of digesting the gel. Suitably the melting or dissolution of the gel is performed with the electrophoresis layer facing upwards and the matrix layer downwards, particularly where the gel is removed by heating.

The matrix of magnetic particles may be tailored to have various forms as desired. The magnetic particles in the matrix may have an affinity to one general type of macromolecules, e.g. all particles carry poly-U residues thereby rendering them capable of binding all mRNA molecules; or alternatively, the particles may have a specific affinity to one specific type of macromolecules, e.g. the particles carry an antibody capable of binding a specific protein. If desired, the matrix may also comprise several different types of particles, each having an affinity to a different species of macromolecules.

The particles may be evenly distributed in the matrix. Thus, if for example all particles are capable of binding immunoglobulins, all separated immunoglobulins in the gel will bind to the matrix and the pattern of immunoglobulins which will be obtained on the magnetic particles matrix will be a replica of that obtained in the gel.

The particles may also be non-uniformly distributed, i.e. concentrated in specific locations of the matrix, e.g., particles having a specific affinity will be located in correspondence to the expected location of the respective macromolecule in the gel.

The present invention further provides methods for the preparation of the matrix of magnetic particles either on a sheet or a solid substrate or as an integral part of the gel.

A matrix of magnetic particles on a sheet in accordance with the non-integral matrix embodiment of the invention may be formed by manually or automatically applying a solution containing magnetic particles to a sheet, as in printing ink on paper or the like, or may be formed by immobilizing magnetic particles on a rigid substrate such as a glass slide with a planar magnet attached on its other side. When using a rigid substrate, it is preferred to place on the magnetic matrix a fine net, e.g. made of tin coated iron, which secures the attachment of the particles to the rigid substrate, and eliminates lateral movement of particles from distant regions towards the collecting device, which may occasionally occur where the attachment of the particles to the substrate is not strong.

In order to form a gel for use in the integral matrix embodiment of the invention, the matrix may first be formed on a sheet, on a rigid substrate or directly on a magnetic plate in a similar manner as described above and then a molten gel is poured on the sheet, rigid substrate or magnetic plate and allowed to harden, whereby the magnetic particles matrix forms one of the external surfaces of the gel. The matrix of magnetic particles can also be formed in the gel by mixing the magnetic particles with the molten gel and prior to hardening of the gel causing the particles to move to one of the surfaces, e.g. by the use of a magnet or several magnets arranged in a desired pattern.

Sheets for use in the non-integral matrix embodiment of the invention and gels for use in the integral matrix embodiment of the invention also form an aspect of the present invention. Another aspect of the invention are kits for carrying out the above method.

The method of the present invention has several advantages as compared to prior art methods:

(1) The biological macromolecules separated in accordance with the invention can be easily recovered by collecting the magnetic particles and then dissociating the macromolecules therefrom. The dissociation can be performed by transferring the magnetic particles into small volumes of suitable solutions with a very small loss of the macro-molecules.

(2) Where the separation of the macromolecules is performed as part of an analysis, the feature that only macromolecules of interest are transferred to the matrix of magnetic particles which is then further analyzed, considerably lowers the background signals which can otherwise be created by other molecules. Accordingly, analysis performed in accordance with the present invention yields a more accurate result, which can more easily be interpreted.

(3) The method of the present invention, allows also multiple probing of the separated macromolecules. In accordance with prior art methods, the binding of the separated macromolecules to the substrate in which the probing was performed, e.g. a nitrocellulose sheet, was weak and consequently it was generally not possible to carry out multiple probing since after each probing it was necessary to wash the matrix which brought about a considerable loss of the tested macromolecules from the matrix. In accordance with the present invention, owing to the fact that the macromolecules of interest are bound with a high affinity to the particles in the matrix which are in turn immobilized, washing of the magnetic matrix will result in only a very minimal loss of the macromolecules, whereby multiple washes and hence multiple probing becomes possible.

(4) In accordance with the method of the invention, each type of macromolecules may be easily separated from the rest and may then undergo separate treatments, e.g. different types of probing, etc.

(5) When using the integral embodiment of the invention, it is possible to recover from the gel many bands of separated macromolecules at once, which eliminates the need of prior art method to elute from the gel (by pressure, vacuum, electricity or dissolvent) each band of macromolecules separately.

DESCRIPTION OF THE DRAWINGS

FIG. 1 is a schematic representation of the separation of macromolecules in accordance with the invention by the use of three different types of magnetic particles' matrix: (a) the matrix consists of longitudinal bands of magnetic particles, the particles in each band having specific affinity to different macromolecules; (b) the matrix consists of a transverse band of particles having specific affinity to one type of macromolecules; and (c) the magnetic particles have general affinity to macromolecules of a certain kind, e.g. to all proteins, and are evenly distributed throughout the matrix. After contacting an electrophoretogram either a specific species of macromolecules in (a) or (b), or all the macromolecule in (c) become immobilized on the matrix. In (b) only macromolecules of a specific molecular weight or specific isoelectric point become immobilized on the gel.

FIG. 2 is a schematic representation of the contacting of the magnetic particles with the electrophoretically separated macromolecules in accordance with the integral matrix embodiment of the invention. A gel 1 with an electrophoretogram 2, shown in FIG. 2(a), is placed, as shown in FIG. 2(b), on a heating plate 4, its matrix layer, with its magnetic paricles 3 arranged in lanes, facing downward, and its electrophoretic layer with the electrophoretogram 2 facing upwards, and a planar magnet 5 is placed on its upper face (for purpose of illustration, the width of the gel is out of proportion). The magnetic particles 3 are attracted to magnet 5 and consequently upon heating of plate 4 and melting of the gel as shown in FIG. 2(c) the particles are not washed away and eventually come into contact with the macromolecules in the electrophoretogram and finally the matrix with the attached macromolecules (at times with some residual gel between the particles) becomes immobilized on magnet 5, as shown in FIG. 2(d). Where the particles have affinity to only a specific species of macromolecules after washing only that specific species remains in the matrix as shown in FIG. 2(e).

FIG. 3 shows an embodiment of the invention in which use is made of a net to enhance immobilization of the magnetic particles to the planar magnet and in order to avoid lateral movement of the particles during collection. As shown in FIG. 3a, a magnetic particles' matrix 10 is formed on a solid substrate 11 the particles being immobilized by means of a planar magnet 12 attached to the substrate's other face. A net 13, preferably made of a ferromagnetic substance is placed on the matrix. (If desired, the sequence of operation may also be reversed: first placing the net and then forming the matrix of magnetic particles). A gel 14 with an electrophoretogram may then be placed onto the net and the macromolecules from the electrophoretogram can then be blotted onto the matrix. The net ensures that the particles will not stick to the gel. Furthermore, as shown in FIG. 3b, the particles carrying a specific type of macromolecules are confined to the holes of the net which facilitates their isolation.

FIG. 4 shows the isolation of particles from a specific hole in the net from the matrix. As shown in FIGS. 4(a) and 4(b), a tapered electromagnetic device 20 collects magnetic particles from a specific hole 21 in the net the particles 22 attached to device 20 as shown in FIG. 4(b) are then transferred into a small vessel 23 placed on top of a magnet 24. By turning off the electromagnet of device 20, the particles 22 collect inside vessel 23 as shown in FIG. 4(c) and then the macromolecules can be recovered from the magentic particles as shown in FIG. 4(d).

DETAILED DESCRIPTION OF THE INVENTION

The biological macromolecules to be separated in accordance with the invention may be proteins, glycoproteins, peptides, DNA molecules and RNA molecules.

The magnetic particles may be particles having a wide range of diameters, particles having a diameters in the range of 100-1500 nm being preferred. Relatively larger particles are preferred when using a rigid substrate in the non-integral embodiment of the invention, so that enough magnetic force is applied to them to ensure their immobilization. The magnetic particles comprise a core made of a magnetic substance such as ferrous oxide and optionally having a coating which confer the particles binding specificity. Suitable particles are, for example, BioMag TM (Advanced Magnetics Inc., Cambridge, Mass., USA). Various types of BioMag TM particles are available having each an affinity to a different specific species of biological macromolecules.

Figure 1A:
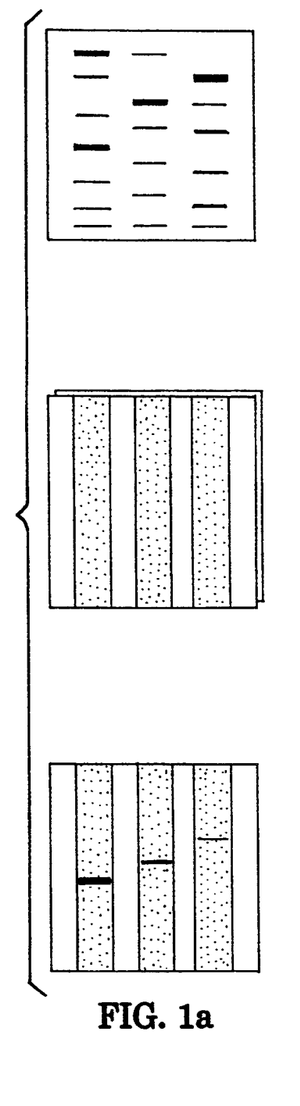
Figure 1B:
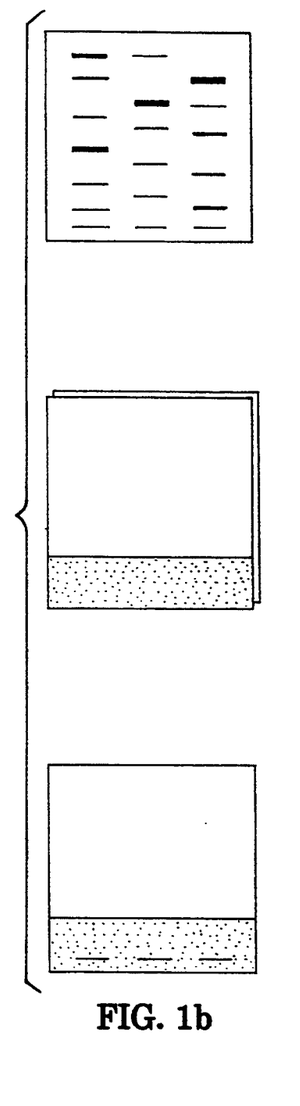
Figure 1C:
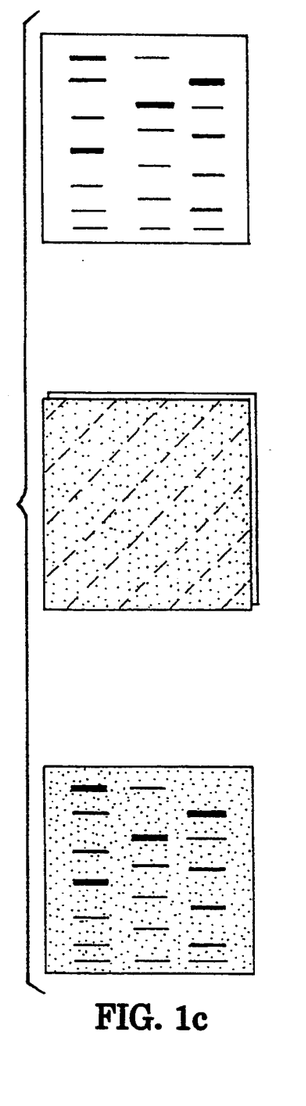
Figure 2A:
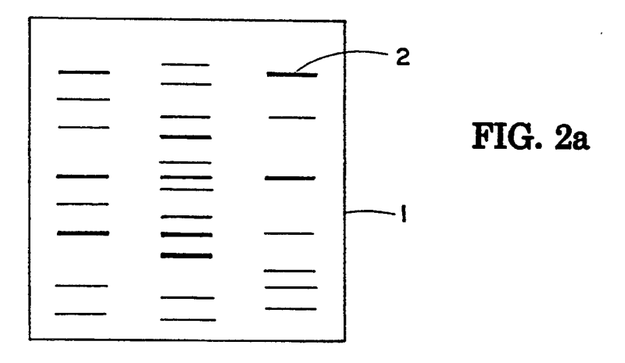
Figure 2B:
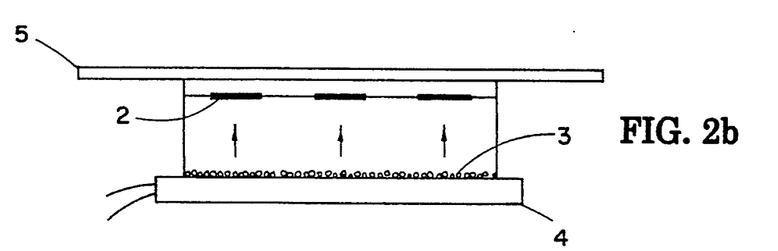
Figure 2C:
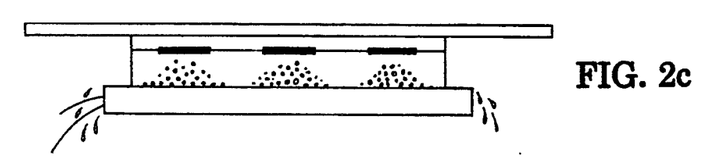
Figure 2D:
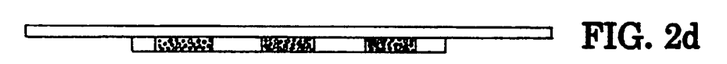
Figure 2E:
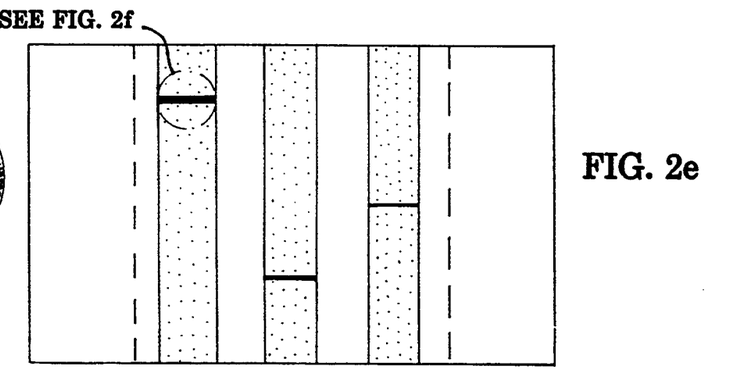
Figure 2F:
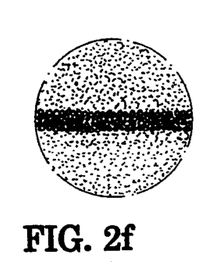
FIG. 2f is an enlarged view of the circled region illustrated in FIG. 2e.

The magnetic particles may have a uniform distribution pattern in the matrix (FIG. 1(c)) or may be non-uniformly distributed, e.g. in a pattern of strips of particles (FIGS. 1(a) and (b)). The strips may, for example be verticial, each of the strips corresponding to a lane in the gel (FIG. 1(a)) which is suitable for collecting all macromolecules in a sample present in a single lane of the electrophoretogram having the same binding specificity. Another example is essentially horizontal strips (FIG. 1(b)) each strip having affinity to a specific species of macromolecules (based on a prior knowledge on the expected location of the respective species in the gel) which is suitable for collecting only such macromolecules having a specific molecular weight in all samples being run simultaneously or to collect proteins having similar isoelectric points when the proteins are separated by the isoelectric focusing method. Where the exact location of a certain species of macromolecules in the gel is not known, the strips of magnetic particles may be diagonal, running through all the possible regions where the desired macromolecules may be present or arranged in horizontal strips at various levels throughout the electrophoretogram. It is possible also to have several kinds of strips of varying specificities arranged in an alternating pattern along the gel.

The electrophoretically separated molecules are transferred to the matrix of magnetic particles in the non integral mode by blotting techniques well-known in the art, such as vacuum blotting, pressure blotting, electroblotting, capilliary blotting. A specific type of pressure blotting is magnetic blotting, in which the sheet containing the magnetic matrix is placed on one surface of the gel with a flat magnet behind the sheet. A board of metal such as iron is placed on the other surfaces of the gel. While the iron board is drawn to the flat magnet, the gel is squeezed between them and the separated molecules transferred to the paper.

In the integral embodiment the molecules are transferred to the magnetic particles by dissolving, melting or digesting the gel and magnetically pulling the magnetic particles towards the separated macromolecules by an inter-layer blotting (FIG. 2).

Figure 4:
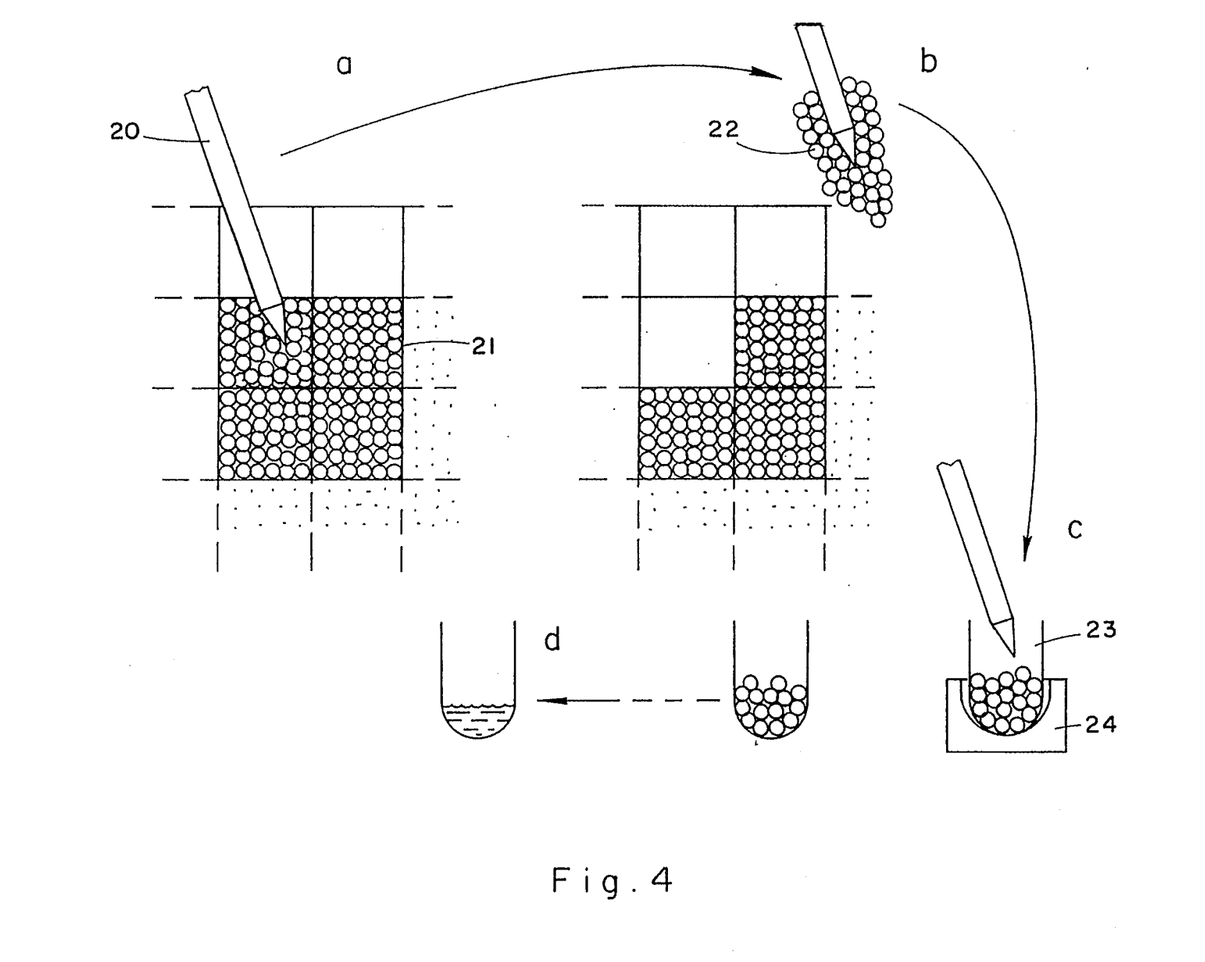

Separated molecules which are bound to the magnetic particles can be subjected to various analytical probings such as testing the binding to monoclonal antibodies bound to certain markers, reacting with various enzymes, contacting with labeled complementary DNA fragments, staining with specific dyes such as ethidium bromide and the like, as the case may be. Some dyes may at times be undetectable on the particles in view of the dark color of the latter. In order to facilitate indentification of a band on the matrix in the non-integral embodiment, particularly where the substrate holding the magnetic particles is a sheet such as paper or nitrocellulose, it is useful to leave portions of the substrate free of magnetic particles. Such free areas will adsorb the same macromolecules as adjacent particles. Thus staining, which will be visible on areas which do not contain the particles will indicate the identity of the macromolecules adsorbed to adjacent particles. Therefore, it is preferable at times not to apply the particles in a continuous layer but rather in the form of strips or dots so as to leave areas of the sheet devoid of any particles throughout the matrix.

Where it is desired to recover the separated macromolecules, the magnetic particles to which these macromolecules are bound are collected. The particles may, for example, be collected by a tapered magnetic collecting device (FIG. 4). Such a collecting device may suitably comprise an electromagnet allowing the attachment and release of the particles in a controlled manner. If the magnetic particles are adsorbed on a sheet, they may be collected by controllably applying a suitable solvent such as water to a chosen location of the matrix so as to loosen the adsorbance of the particles to the sheet without completely disconnecting them therefrom and then collecting them by a tapered magnetic device as above. The collection of the particles may be automated, e.g. by the use of a magnetic collecting device whose position is controlled by a servo x-y machine.

The magnetic particles may then be transferred to small vessels such as a well of a microwell plate. In order to ensure that the particles are not lost, a magnet can be placed below the vessel in which the particles are placed (FIG. 4(d)). The bound macromolecules can be dissociated from the particles by any means known per se depending on the nature of the specific binding between the particles and the macromolecules. Finally, the free magnetic particles can be removed by the use of a magnet, by centrifugation by filtration, etc., and, if desired, can be washed and recycled for further use. It is somtimes advantageous to keep the macromolecules bound to the particle, such as, for example, where the separated molecule is a DNA molecule to be subjected to PCR treatment, in which case it is preferable to have one strand immobilized. (Hultman T., et al., *Bio Techniques*, 10 (1), 84–93, (1991)).

The matrix of magnetic particles can be formed by adsorption or absorption of the particles to a suitable sheet such as a filter paper, nitrocellulose sheets, pergameneous material sheet, cellulose acetate and xerographic paper. It is at times preferable to use sheets to which the adsorption of the particles is relatively weak in order to facilitate the collection of the particles after the blotting stage, nitrocellulose or cellulose acetate sheet being especially preferred for such a purpose. Where such sheets are used, in order to ensure immobilization of the particles to such sheets, a magnet, e.g. a planar magnetic substrate is placed behind the sheet.

In addition to weakly adsorbing sheets, it is also possible to use at times sheets which strongly absorb or adsorb the magnetic particles. Such may for example be xerographic paper. Xerographic paper generally has pores and the particles which enter such pores strongly stick thereto and cannot easily be removed. Thus, while most of the particles from the paper can be removed by scraping or by the use of certain solvents, some of the particles will always remain absorbed thereto. Thus, the removed particles can be used for the recovery of the separated macromolecules and the particles which remain absorbed in the paper can then be assayed, by single or multiple probing.

The magnetic particles can be applied to the sheet manually or using an automated printer. The printer can use simultaneously several "pens" each containing a solution of particles having a different binding affinity.

Figure 3A:
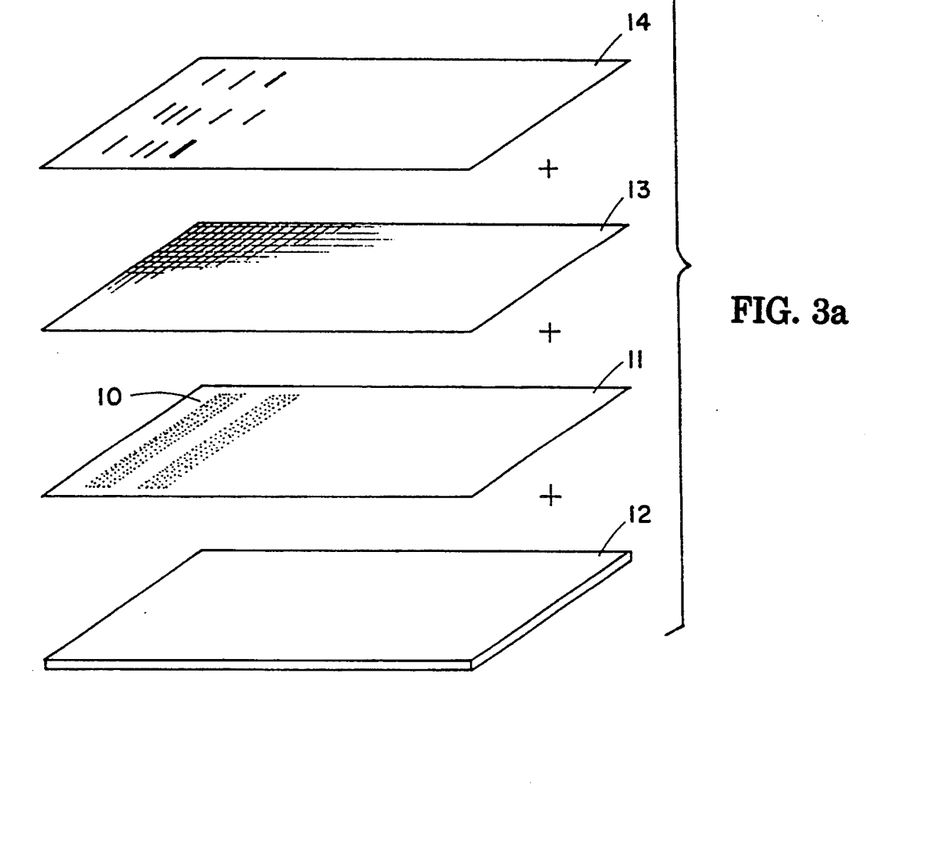
Figure 3B:
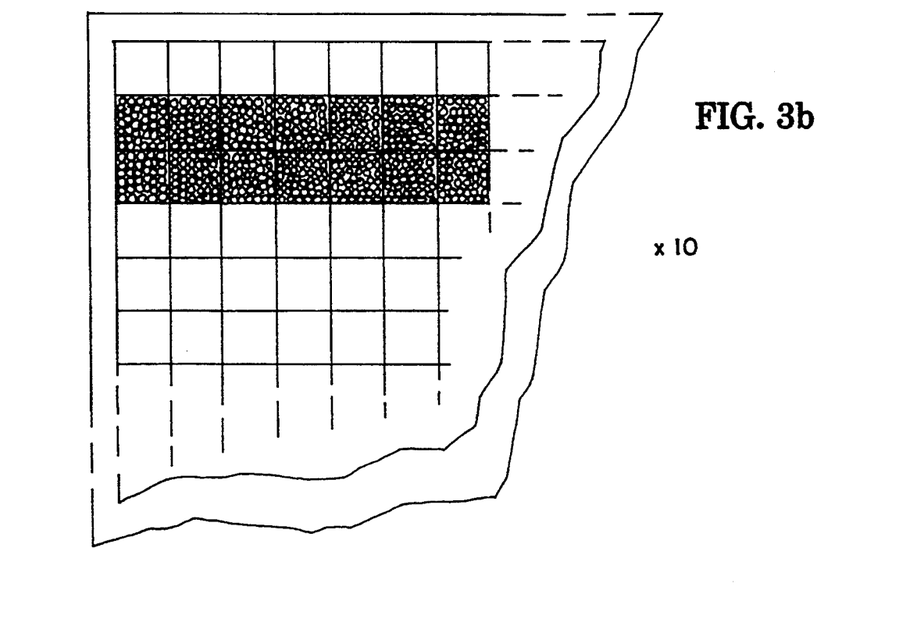

When performing the non-integral embodiment, particularly where the substrate holding the magnetic particles' matrix only weakly holds the particles, it is preferred to place a net on the matrix (FIG. 3). Such a net ensures that the particles will not stick to the gel and further ensures a localized collection of particles as it avoids lateral movement of distant particles during collection. Where the net is made of a ferromagnetic substance, there is formed a local magnetic field inside the holes of the net which holds the particles inside the holes relatively firmly.

The gel to be used in accordance with the present invention may for example be agarose gel or polyacrylamide gel. The matrix of magnetic particles may, in accordance with the integral matrix embodiment, be included as a layer in the gel, close to one of its external surfaces opposite that in which the electrophoresis is performed. As pointed out above, when carrying out this embodiment, contacting the particles with the macromolecules in the electrophoretogram may suitably be performed by gently heating the surface near the matrix layer of the gel while drawing the particles towards a magnet at the surface near the electrophoresis layer of the gel (FIG. 2). As an alternative to melting the gel by heat, the gel may also be dissolved by the use of chaotropic agents such as solutions of high concentrations of potassium iodine, sodium perchlorate or sodium iodine. Even where chaotropic agents are used it is preferred that during dissolution the gel be gently heated to about 45° C. Another possibility is a digestion of the gel, for example, GELASE ™ (Epicentere Technologies, USA) which digests the carbohydrate backbone agarose gel.

The kit of the invention may comprise a gel for use in the integral-matrix embodiment or a gel and a sheet or rigid substrate for use in the non-integral matrix embodiment, the latter optionally accompanied with a net to be placed-on the matrix. The kit may also comprise free magnetic particles for the preparation of the above gel or sheet. In addition, the kit may comprise a flat magnet which is at times suitably lightly colored or coated by an inert substance having a light color so as to provide a contrast for the particles which have a dark color. In addition, the kit may comprise various reagents such as solvents for freeing the particles from the matrix in which they are contained or agents for use in the separation of the macromolecules from the particles, chaotropic agents for dissolving the gel, enzymes for digesting the gel, devices for collecting the particles, microwells with associated magnets below their bottoms, etc.

EXAMPLES

Example I

A. Construction of the Magnetic Matrix

Eight flat square fine tin-coated magnets, 20 mm each side and 4 mm thick (VACODYM ™ 370 HR P/N 66750490, Vacuumschmelze GmbH, Germany) were attached in pairs to give 4 (40 mm×20) mm rectangles. Each of the 4 rectangles was separated from each other by 40 mm×20 mm×2 mm rubber sheets, to form alternating layers of magnets and rubber. This construction forms a box which narrow side has 4 strips of magnets 40 mm long and 4 mm wide, separated by strips of rubber 40 mm long and 2 mm thick and will be referred hereinafter as the "*stripped magnet*".

The above box can also be constructed without use of the rubber strips so its side has a dimension of 40×16 mm or 20×32 mm, which construct will be referred to hereinafer as the "*uniform magnet*".

B. Preparing a Magnetic Particle Matrix Integrated in Agarose

A silicon rubber rectangular frame 1 mm thick, 7×7 cm outer dimension and 5×5 cm inner casting space-was attached, via silicon grease Silicaid, Aidchim Ltd., Israel) to a 7×7 cm clean glass plate. The glass plate was placed on the stripped magnet, prepared as described in A above and heated with a hair dryer. 200 μl from 1 μm diameter superparamagnetic ferrous oxide particles which were not coated with a functional affinity group (Advanced Magentics Inc., USA) were drawn from a 50 mg/ml stock solution and were injected to 3 ml of a 2% aqueous solution of low melting point agarose (A-9414, Sigma Chemical Co., USA) at a temperature of 45° C. and mixed for 1 minuted by a vortex. The agarose was poured into the casting space and then covered with a 7×7 cm hot glass plate. After a few minutes at 35° C.–40° C. the gel was allowed to cool and was left at room temperature for at least one hour. During this time the magnetic particles were drawn to the stripped magnet and a stripped matrix of magentic particles at the bottom layer of the gel was then obtained. The same procedure was repeated with the uniform magnet, whereby a uniformed matrix of magnetic particles was obtained.

If extra support to the gel is desired, an inert polypropylene support net 100 μm thick with a pore diameter of 200 μm may be placed in the casting space prior to pouring of the gel.

C. Isolation of Magnetic Particles

An agarose gel prepared as described above, was placed on a flat magnet of 40×40 mm in size which was constructed with a uniform magnet obtained by placing 4 magnets one beside the other on a flat 7×7 cm tin coated iron plate 0.3 mm thick which was used for extra support. The gel was placed on the magnet so that the layer of magnet particles was facing downwards and its ends were carefully cut; to give a gel size of 40×40 mm. A rectangular rubber frame 2 mm thick, 5×5 cm outer dimension and 3×3 cm inner space was placed on the gel and held by the magnetic force of four 0.5×5.0 cm iron sheets which were placed on it. 2 ml of saturated NaI aqueous solution at 38° C. was poured into the inner space of the rubber frame. After 5 minutes all the gel was dissolved and the solution with the dissolved gel was then poured away by tilting the plate. The stripped or uniform patterns of the magnetic particles were transferred to the uniform magnet with no substantial change. Remainders of wet agarose were washed away and the beads were collected with the aid of a tapered electromagnet.

Example II

Preparation of a Matrix of Magentic Particles as an Integral Part of the Gel

A solution of magnetic particles (EMG 705 Water Base Ferrofluid Ltd., Israel) was manually applied onto the surface of pergameneous paper with the aid of the tip of a glass Pasteur pipette in a pattern of diagonal strips, and left to dry for 1 hr.

The paper was then glued to a glass plate via contact glue or a double face adhesive tape. A silicon rubber rectangular frame, 1 mm thick, 7×7 cm outer dimension and 5×5 cm inner casting space was placed on the glued paper and attached by 4 clips. The glass plate was placed on a gel casting table equilibrated to a temperature of 35° C. A polypropylene support net, 100 μm thick 200 μm pore diameter was placed into the casting space prior to pouring the gel. 3 ml of 2% aqueous solution of agarose low-electroendosmosis (05071, Fluka, Switzerland) in a temperature of 60° C. was poured into the casting space. The gel was covered with a glass plate and left to solidify at room temperature for at least one hour. The resulting gel contained on its surface the replica of the magnetic particles originally formed on the sheet.

Example III

Collecting of Magnetic Particles from a Specific Location in a Matrix

Four magnets as described above were placed on a 7×7×0.3 cm tin coated iron plate in two pairs and separated from one another by a gap of 3 cm. The tin coated iron plate was placed on the magnets and a tin coated iron net having holes in the size of 1 mm was placed on the iron plate and held by the magnetic force of the two pairs of magnets. 1 gr iron powder, 50-150 μm in particle size, was placed on the net and gently spread in the net area above the 3 cm gap between the magnets. The net and magnetic force held the particles so tightly that a wet filter paper placed on the net and pressed by a second tin coated iron plate for 10 min. did not remove any of the particles.

A tapered electromagnet was used to collect the particles from the net. The net enables the collection of particles from each hole of 1 mm in size separately, with no lateral movement of particles from the other holes (see FIG. 4). The tip of the tapered electromagnet was placed inside a well in a microtiter plate fixed on an adapter with a built in matrix of permanent magnets (BioMag Separator 4101S, Advanced Magnetic, Inc., USA). Shutting off the current of the electromagnet caused the transfer of the particles from the electromagnet's tip to the well.

Example IV

A. Formation of a Matrix of Magnetic Particles on a Sheet (i) A 5×5 cm sheet of cellulose acetate (S & S, OE67) 0.45 μm porosity was moistened with distilled water and then attached by adhesion to a 10×10×0.1 cm glass plate. Excess water was discarded and a nylon net with 200 μm holes was attached to the sheet to eliminate movement of the particles. The glass plate was laid on the stripped magnet prepared as in A above, and attached to the matrix by an adhesive tape for extra support.

50 μl of an aqueous suspension of ferrous oxide particles described above in Example I were diluted with 10 ml distilled water and the diluted suspension was sprayed on the nylon net attached to the sheet, from a distance of 3-5 cm, while holding the combinated sheet and glass plate at an angle of 45°-90°. The magnetic particles became attached to the sheet at a striped pattern corresponding to that of the magnet. The sheet was left to dry and drying was enhanced by placing blotting paper or filter paper at the sides of the cellulose acetate sheet. The nylon net was then removed, and the matrix of magnetic particles retained the striped pattern, but each stripe was dotted as a result of the nylon net.

The same procedure was repeated with nitrocellulose sheets (S & S, BA85).

(ii) The solution of ferrous oxide particles described above was drawn into a pipette tip (100 μm tip) by a Nichiryo Model 5000 Pipetor 10-50 μl (Japan) and with the aid of the tip stripes at a desired pattern were applied on a cellulose acetate sheet. By using a volume of 20 μl a line of 4 cm long and 0.5 mm wide and 15 dots of approximately 1 mm diameter each could be drawn.

B. Isolation of Magnetic Particles

A filter sheet prepared as described above (A(i)) was attached to a flat magnet, with the matrix of magnetic particles facing towards the magnet. A rubber frame having an inner space of 3×3×0.2 cm was attached to the sheet and 2 ml acetone 100% was added into the inner space. After 5 min. the acetone was discarded and replaced by 2 ml fresh acetone and the procedure was repeated 5 times. The particles remained on the flat magnet in their original pattern and could be collected with the aid of a tapered electromagnetic device. Magnetic particles were bound to the tip of the device because of the very high local magnetic field exerted upon them. The tip of the electromagnetic collecting device was then placed inside a well in microtiter plate fixed on an adaptor with a built in matrix of permanent magnets, and the current activating the electromagnet was shut off and consequently the particles were pulled from tip of the collecting device into the well.

We claim:

1. A method for isolating a specific species of biological macromolecules from a sample involving separating said macromolecules by electrophoresis, thereby obtaining an electrophoretogram of said macromolecule, said method being characterized in that:

said electrophoretogram is contacted with a planar matrix of magnetic particles having binding specificity to one or more specific species of biological macromolecules, whereby said one or more specific species bind to particles in the matrix at the location of the matrix, which corresponds essentially to the location of said one or more specific species in said electrophoretogram, wherein said macromolecules are recovered from the matrix by collecting magnetic particles from the matrix and then separating the macromolecules from the particles.

2. A method according to claim 1, wherein the particles are collected by means of a tapered magnetic collecting device.

3. A method according to claim 1, wherein the matrix of magnetic particles is formed on a flat substrate and the contact between the particles and said macromolecules is effected by blotting the macromolecules from the electrophoretogram to the matrix.

4. A method according to claim 3, wherein the flat substrate is a glass, iron or plastic board and the magnetic particles are immobilized on the substrate by means of a magnetic force.

5. The method of claim 4 wherein said substrate has immobilized thereon a plurality of magnetic particles having a binding affinity to one or more specific species of molecules, and wherein said particles are immobilized by means of a magnetic force.

6. A method according to claim 1, wherein the matrix of magnetic particles is formed as a layer in the gel used for electrophoresis, which layer is different than the one in which the macromolecules are electrophoresed, the contact between the particles and the macromolecules following electrophoresis is effected by inter-layer blotting in the gel.

7. A method according to claim 1, wherein the matrix of magnetic particles is formed as a layer in the gel used for electrophoresis, which layer is different than the one in which the macromolecules are electrophoresed, the contact between the particles and the macromolecules following electrophoresis being effected by dissolving, melting or digesting the gel starting from the surface near the layer of the gel containing the magnetic particles matrix while drawing the particles towards the other surface by means of magnetic attraction to a body adjacent the surface of the gel near the electrophoresis layer.

8. A method according to claim 1, wherein all the magnetic particles have the same binding affinity.

9. A method according to claim 1, wherein the matrix comprises particles having different binding affinities.

10. A method according to claim 1, wherein the particles are evenly distributed in the matrix.

11. A method according to claim 1, wherein the particles are concentrated in specific locations of the matrix.

12. A method according to claim 11, wherein the particles are arranged in strips.

13. A method according to claim 1, wherein the magnetic particles are arranged in strips, each strip comprising particles having all the same binding affinity.

14. The method of claim 1 wherein said planar matrix comprises a sheet having immobilized thereon a plurality of magnetic particles having a binding affinity to one or more specific species of molecules, the immobilization of said particles onto said sheet being by means of absorption.

15. A matrix of magnetic particles having binding affinity to one or more specific species of macromolecules, formed as a layer in a gel intended to be used for electrophoresis, which layer is distinct from the layer in which the electrophoresis is performed.

16. A gel for use in electrophoresis comprising a matrix of magnetic particles formed on a layer in said gel which is another layer than that in which the electrophoresis is performed.

* * * * *